United States Patent [19]

Kaiser et al.

[11] Patent Number: 4,707,485
[45] Date of Patent: Nov. 17, 1987

[54] SUBSTITUTED TE[1]TRAHYDROISOQUINOLINE DERIVATIVES HAVING β-ADRENERGIC RECEPTOR ACTIVITY

[75] Inventors: Carl Kaiser, Haddon Heights; Lawrence I. Kruse, Haddonfield, both of N.J.

[73] Assignee: Smithkline Beckman Corporation, Philadelphia, Pa.

[21] Appl. No.: 877,932

[22] Filed: Jun. 24, 1986

[30] Foreign Application Priority Data

Jul. 23, 1985 [GB] United Kingdom ............... 8518634

[51] Int. Cl.$^4$ ..................... A61K 31/47; C07D 217/20
[52] U.S. Cl. .................................... 514/307; 546/139; 546/144
[58] Field of Search ................. 546/139, 144; 514/307

[56] References Cited

U.S. PATENT DOCUMENTS 3,910,915 10/1975 Yonan ................................. 260/247
4,514,569 4/1985 Hendrickson ...................... 546/146

OTHER PUBLICATIONS

Kiyomoto, A. et al., *Arzneim-Forsch.* (Drug. Res.), 20: 46–52 (1970).
Yamoto et al., Tetrahedron Supp. 8, pt. 1, 129 (1966).
Iwasawa, Y. and Kiyomoto, A., *Jap. J. Pharmacol.*, 17: 143–152 (1967).
Dyke, S. F. et al., Tetrahedron 29: 857–862.
Perchonock, C. D. et al., *J. Org. Chem.*, 45: 1950–1953 (1980).
Chemical Abstract, 52: 3832b (1956).
Chemical Abstract, 90: 121442 (1978).
Chemical Abstract, 60: 79926 (1964).

*Primary Examiner*—Robert T. Bond
*Assistant Examiner*—Patricia L. Morris
*Attorney, Agent, or Firm*—Vincent L. Fabiano; Stuart R. Suter; Alan D. Lourie

[57] ABSTRACT

Compounds having the formula

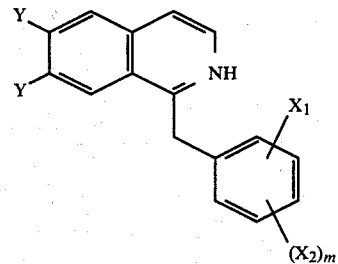

are β-adrenergic receptor antagonists. Also disclosed are pharmaceutical compositions and methods for producing β-adrenergic receptor antagonistic activity in animals including man.

8 Claims, No Drawings

SUBSTITUTED TE[1]TRAHYDROISOQUINOLINE DERIVATIVES HAVING β-ADRENERGIC RECEPTOR ACTIVITY

FIELD OF THE INVENTION

The present invention relates to substituted tetrahydroisoquinoline derivatives which have β-adrenergic receptor activity, processes for their preparation, intermediates used in their preparation, pharmaceutical compositions containing them, and their use in therapy.

Compounds which antagonize β-adrenergic receptors ("β-blockers") are used in the treatment of cardiovascular diseases, for example hypertension, angina pectoris, arrhythmias and obstruction of cardiac outflow. They are also useful in the treatment of glaucoma and migraine headache. Such compounds in common use include, for example, propranolol.

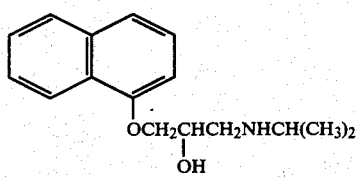

A compound which is known to have the opposite effect that is, to produce a stimulation of the β-adrenergic receptors and to have bronchodilator activity (Kiyomoto, A., et al., Arzneim.-Forsch. (Drug Res.), 20:46–52, 1970) is trimetoquinol which has the following structure

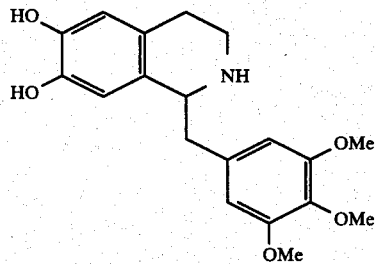

It has now been found that certain compounds structurally related to trimetoquinol have significant β-blocking activity while having little or no β-receptor stimulating activity and are of use in the treatment of cardiovascular diseases, for example hypertension and other disorders associated with β-blocking activity.

The present invention therefore provides in a first aspect a compound of structure (I)

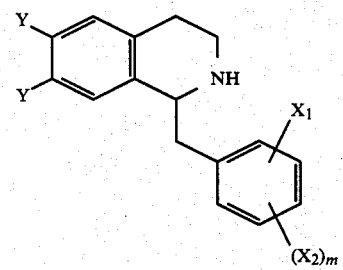

in which

Y is halogen;
$X_1$ is $C_{1-4}$ alkoxy;
m is 0 to 4; and
$X_2$ is $C_{1-4}$ alkoxy, halogen or $C_{1-4}$ alkyl, provided that
(i) when m is 1, 3 or 4, each $X_2$ is $C_{1-4}$ alkoxy; and
(ii) when m is 2, at least one $X_2$ is $C_{1-4}$ alkoxy, or a pharmaceutically acceptable acid addition salt thereof.

Suitably, m is 1, 3 or 4, and each $X_2$ is $C_{1-4}$ alkoxy.

Preferably, m is 2, one $X_2$ is $C_{1-4}$ alkoxy and the other is $C_{1-4}$ alkoxy, halogen or $C_{1-4}$ alkyl. Most preferably m is 2 and both substituents $X_2$ are $C_{1-4}$ alkoxy.

$C_{1-4}$ alkyl groups, alone or as part of another group (for example $C_{1-4}$ alkoxy) can be straight or branched, for example methyl, ethyl, n-propyl, i-propyl, i-butyl, s-butyl or n-butyl. Preferably $C_{1-4}$ groups are methyl.

Preferably $C_{1-4}$ alkoxy groups are methoxy or ethoxy.

Preferably halogen groups are chlorine or bromine.

A particular compound of the present invention is a compound of structure (I) in which m is 2, and $X_1$ and both substituents $X_2$ are methoxy, namely, 6,7-dichloro-1-(3,4,5-trimethoxybenzyl)-1,2,3,4-tetrahydroisoquinoline.

It will be appreciated that the carbon atom of the isoquinoline ring to which the substituted benzyl group is attached is an asymmetric center and thus compounds of formula (I) are optically active compounds. As such the compounds will exist as two optical isomers (enantiomers).

Both the pure enantiomers, racemic mixtures (50% of each enantiomer) and unequal mixtures of the two are included within the scope of the present invention.

In a further aspect of the present invention there are provided processes for the preparation of compounds of structure (I). Compounds of structure (I) can be prepared by reduction of a compound of structure (II)

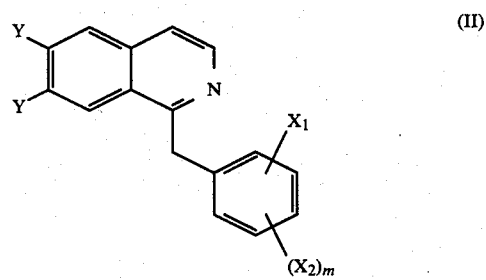

in which Y, $X_1$, $X_2$ and m are as described for structure (I). Suitable reducing agents include, for example, borane in tetrahydrofuran.

In a further aspect there is provided compounds of structure (II) which are useful in the preparation of the compounds of structure (I).

Compounds of structure (II) can be prepared from compounds of structure (III):

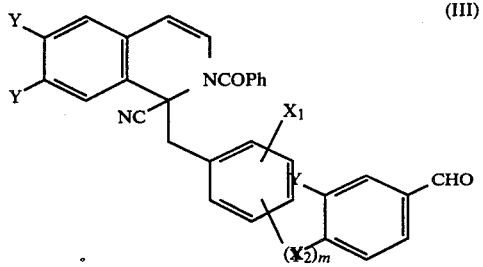

in which Y, $X_1$, $X_2$ and m are as described for compound (I), by reaction with, for example benzyl triethylammonium.

Compounds of structure (III) can be prepared by reaction of a compound of structure (IV) and a compound of structure (V)

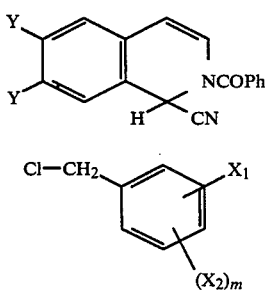

in which Y, $X_1$, $X_2$ and m are as described for structure (I) and Ph is phenyl.

Compounds of structure (IV) can be prepared by reaction of compounds of structure (VI)

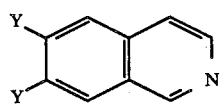

in which Y is halogen, with a suitable acid chloride, for example benzoyl chloride in potassium cyanide, optionally in the presence of a crown ether, for example 18-Crown-6.

The precursor isoquinolines of structure (VI) can be prepared by standard procedures, for example as described in Scheme 1 below.

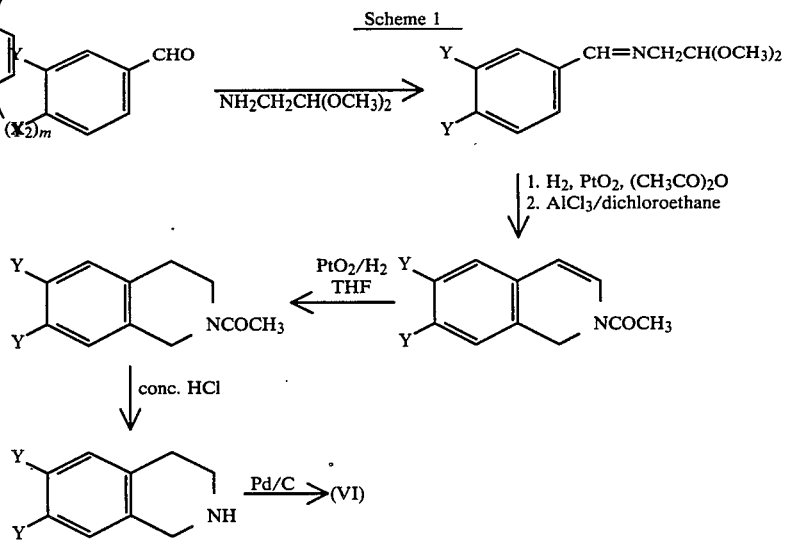

The pharmaceutically acceptable acid addition salts of the compounds of structure (I) are formed with strong or moderately strong organic or inorganic acids by methods known to the art. For example, the base is reacted with an inorganic or organic acid in an aqueous miscible solvent such as ethanol with isolation of the salt by removing the solvent or an an aqueous immiscible solvent when the acid is soluble therein, such as ethyl ether or chloroform, with the desired salt separating directly or being isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

In a further aspect of the present invention there is provided compounds of structure (I) for use as therapeutic agents. The compounds of structure (I) and their pharmaceutically acceptable acid addition salts have been found to antagonize β-receptors. They are of use in the treatment of cardiovascular diseases, for example hypertension, angina pectoris, arrhythmias and obstruction of cardiac outflow, as well as other disorders, for example, migraine headache and glaucoma.

In therapeutic use, the compounds of the present invention are usually administered in a standard pharmaceutical composition. There is therefore provided in a further aspect of the present invention pharmaceutical compositions comprising a compound of structure (I) or a pharmaceutically acceptable acid addition salt thereof in association with a pharmaceutically acceptable carrier.

The compounds of structure (I) and their pharmaceutically acceptable acid addition salts may be administered in a standard manner for the treatment of the indicated diseases, for example by oral, parenteral, rectal, ocular, or transdermal administration.

For oral or parenteral administration the compounds can be incorporated into convenient dosage unit forms such as capsules, tablets or injectable preparations.

Pharmaceutical carriers which can be employed can be solid or liquid. Solid carriers include, among others, lactose, terra alba, sucrose, talc, gelatin, agar, pectin, acacia, magnesium stearate, and stearic acid. Liquid carriers include, among others, syrup, peanut oil, olive oil and water. Similarly, the carrier or diluent may include any time delay material, such as glyceryl monostearate or glyceryl distearate, along or with a wax. The amount of solid carrier will vary widely but, preferably, will be from about 25 mg to about 1 g per dosage unit. If a liquid carrier is used, the preparation will be in the form of a syrup, emulsion, soft gelatin capsule, sterile injectable liquid such as an ampoule, or an aqueous or non-aqueous liquid suspension.

For rectal administration the compositions comprise a binder and/or lubricating agent, for example polymeric glycols, gelatins, cocoa butter or other low-melting vegetable waxes or fats.

For ocular administration the compositions comprise a buffered isotonic liquid, for example isotonic sodium chloride.

For transdermal administration, the compositions comprise a conventional aqueous or non-aqueous vehicle, for example a cream, ointment, lotion or paste or can be in the form of a medicated plaster, patch or membrane.

The pharmaceutical preparations are made following conventional techniques of a pharmaceutical chemist involving mixing, granulating and compressing, when necessary, for tablet forms, or mixing, filling and dissolving the ingredients, as appropriate, to give the desired oral or parenteral products.

Doses of the present compounds in a pharmaceutical dosage unit will be an effective amount, that is, a nontoxic quantity selected from the range of 0.1–1000 mg/kg of active compound, preferably 10–100 mg/kg. The selected dose is administered to a patient in need of treatment from 1–5 times daily, orally, rectally, by injection or by infusion. Parenteral administration, which uses a low dose, is preferred. However, oral administration, at a higher dose, can also be used when safe and convenient for the patient. For ocular use, sterile isotonic solutions of an acceptable acid addition salt may be administered directly into the eye.

The following examples are illustrative of preparation of compounds of the invention or intermediates thereof. All temperatures and melting points (m.p.) are in degrees Celsius (°C.).

EXAMPLE 1

Preparation of 6,7-dichloro-1-(3,4,5-trimethoxybenzyl)-1,2,3,4-tetrahydroisoquinoline fumarate (i) A stirred mixture of 6,7-dichloro-,1,2,3,4-tetrahydroisoquinoline (6.2 g, 30 mmole), prepared by the procedure of C. Perchonock, et al., J. Org. Chem., 45, 1950, (1980), 0.6 g of 10% palladium-on-carbon and 100 ml of p-cymene was heated at reflux, under nitrogen, for 20 hours. The mixture was filtered and the filtrate was extracted with 2N hydrochloric acid. The acid extract was washed with ether, then it was made alkaline with 10N sodium hydroxide. The mixture was extracted with ethyl acetate. After the organic extracts were washed with water and dried (MgSO$_4$), they were concentrated to give a solid residue. Recrystallization from ethanol afforded 6,7-dichloroisoquinoline hydrochloride as colorless crystals, m.p. 227°–228° C.

(ii) To a stirred suspension of 1.7 g (8.6 mmole) of 6,7-dichloroisoquinoline hydrochloride in 12 ml of methylene chloride was added 0.11 g (0.43 mmole) of 18-crown-6 followed by a solution of 1.67 g (26 mmole) of potassium cyanide in 12 ml of water. The mixture was stirred vigorously under nitrogen for 30 minutes and then a solution of 2.4 g (17.2 mmole) of benzoyl chloride in 10 ml of methylene chloride was added dropwise. After the reaction mixture was stirred at ambient temperature, under nitrogen for 3 hours, an additional 50 ml of methylene chloride and 50 ml of water was added. The organic phase was separated, washed successively with water, 5% aqueous sodium bicarbonate solution, water and brine. The solution was dried over magnesium sulfate and concentrated. The resulting oil was triturated with methanol at 0° C. to give 2-benzoyl-6,7-dichloro-1-cyano-1,2-dihydroisoquinoline, m.p. 194°–196° C.

(iii) To a stirred solution of 1.7 g (5.17 mmole) of 2-benzoyl-6,7-dichloro-1-cyano-1,2-dihydroisoquinoline, 1.16 g (5.37 mmole) of 3,4,5-trimethoxybenzyl chloride and 0.118 g (0.517 mmole) of benzyltriethylammonium chloride in 25 ml of toluene, under nitrogen, was added 7.2 ml of 50% sodium hydroxide solution. The mixture was stirred vigorously at ambient temperature for 2 hours, and then 25 ml of water and 25 ml of methylene chloride was added. The organic layer was separated, washed with water, dried over magnesium sulphate and concentrated to give 2-benzoyl-1-(3,4,5-trimethoxybenzyl)-6,7-dichloro-1-cyano-1,2-dihydroisoquinoline, m.p. 193°–195° C., after recrystallization from acetonitrile.

By replacement of the 3,4,5-trimethoxybenzyl chloride used in this reaction with other benzyl chlorides of the general structure

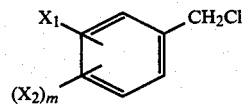

other compounds of the general structure (III) are prepared.

(iv) Benzyltriethylammonium chloride (0.118 g, 0.517 mmole) was added to a solution of 2.3 g (4.5 mmole) of 2-benzoyl-1-(3,4,5-trimethoxybenzyl)-6,7-dichloro-1-cyano-1, 2-dihydroisoquinoline in 40 ml of toluene. The stirred solution was flushed with nitrogen and then 19 ml of 50% sodium hydroxide solution was added in one portion. The reaction mixture was stirred and refluxed under nitrogen for 1.5 hours; it was then cooled and 25 ml of water and 25 ml of ethyl acetate were added. The organic layer was separated, washed (water, brine), dried (magnesium sulfate) and concentrated. The residue in a small volume of methanol was acidified with hydrogen chloride and ether was added to give 6,7-dichloro-1-(3,4,5-trimethyoxybenzyl)isoquinoline hydrochloride as white crystals, melting at 211°–212° C., after recrystallization from methanol-ether.

Utilization of other compounds of structure (III) afforded the corresponding 1-(substituted benzyl) isoquinolines (II).

(v) A solution of 1.8 g (4.3 mmole) of 6,7-dichloro-1-(3,4,5-trimethoxybenzyl)isoquinoline hydrochloride in 25 ml of water was made alkaline with 2.5N sodium hydroxide. The mixture was extracted with ether. The ether solution was washed with water, dried over magnesium sulfate and concentrated. To a solution of the residual base in 5 ml of tetrahydrofuran was added 18 ml of a 1M solution of borane in tetrahydrofuran. The solution was refluxed for 6 hours under nitrogen, an additional 5 ml of the borane solution was added and refluxing was continued for 1.5 hours longer. After the solution was cooled to 10° C., 10 ml of methanol was added cautiously, and the solution was evaporated to dryness. The resulting residue was mixed with 20 ml of 2.5N hydrochloric acid and refluxed for 30 minutes. The solution was cooled to 20° C., made alkaline. with 10N sodium hydroxide and the mixture was extracted with ethyl acetate. The organic extracts were washed with water, dried over magnesium sulfate and concentrated. A solution of the residue in acetonitrile was treated with excess fumaric acid to give 6,7-dichloro-1-(3,4,5-trimethoxybenzyl)-1, 2,3,4-tetrahydroisoquinoline fumarate, m.p. 163° C., after recrystallization from acetonitrile.

Similar reduction of other isoquinolines of the general structure (II) affords the corresponding compounds of structure (I).

A similar sequence may be used to prepare compounds of general formula (I) where Y=F, Br. In this case requisite tetrahydroisoquinoline starting materials may be prepared according to the procedure of C. Perchonock, et al., J. Org. Chem., 45, 1950, (1980) (Scheme 1).

EXAMPLES 2–11

Using the procedure substantially as described in Example 1, the following compounds are prepared.

TABLE 1

| Example | Y | $X_1$ | m | $X_2$ |
|---------|----|---------------------|---|------------------------|
| 2 | Cl | 2-CH$_3$O | 0 | |
| 3 | Cl | 2-CH$_3$O | 1 | 4-CH$_3$O |
| 4 | Cl | 3-CH$_3$O | 1 | 4-CH$_3$O |
| 5 | Cl | 2-CH$_3$O | 2 | 4-Br,5-CH$_3$O |
| 6 | Cl | 2-CH$_3$O | 2 | 4-CH$_3$,5-CH$_3$O |
| 7 | Cl | 2-CH$_3$O | 3 | 3,4,5-CH$_3$O |
| 8 | Cl | 2-CH$_3$O | 4 | 3,4,5,6-CH$_3$ |
| 9 | Br | 3-CH$_3$O | 2 | 2-CH$_3$O |
| 10 | F | 3-CH$_3$O | 2 | 2-CH$_3$O |
| 11 | I | 3-CH$_3$O | 2 | 2-CH$_3$O |

The β-blocking activity of the compounds of structure (I) can be assessed in a test for inhibition of isoproterenol-induced enhancement of the rate of contraction of guinea pig atrial pairs in vitro.

EXAMPLE 12

Inhibition of isoproterenol-induced enhancement of constricted guinea pig atria

A guinea pig (500–700 g) was injected with sodium pentobarbital (50 mg/kg, ip). When anesthetized, the heart was removed and placed in cold (5°–10° C.), oxygenated Krebs-Hensleit solution. The ventricles and adipose tissue were carefully cut away to leave the atria as an intact pair. A thread was tied to the apex of each atrium and the tissue suspended in a 50 ml tissue bath, attached to a force-displacement transducer. A diastolic tension of 1 g was maintained. Atrial contraction rate was measured using biotachometer, driven by the transducer amplifier.

A 30 minute stabilization period was allowed before obtaining the first dose response curve, during which time the tissue was washed several times with fresh solution. A concentration-response curve to isoprotererol was then determined, increasing agonist concentrations when the rate response to the previous dose had stabilized. After this determination, any β-antagonist activity of the test compound was measured via a concentration-response curve. A concentration of test compound which produced no β-response was then allowed to remain in the tissue bath while the curve for isoproterenol was repeated. The receptor dissociation constant ($K_B$) as a β-antagonist was determined using the formula $$K_B = \frac{\text{Antagonist Concentration}}{\text{Dose Ratio} - 1}$$

where the Dose Ratio equals the EC$_{50}$ for isoproterenol in the presence of antagonist divided by the control EC$_{50}$ for isoproterenol.

Composition of Krebs-Hensleit Solution = NaCl, 119 mM; NaHCO$_3$, 25 mM; KCl, 4.7 mM; MgSO$_4$, 1.5 mM; KH$_2$PO$_4$, 1.2 mM; CaCl$_2$, 2.5 mM; glucose, 11 mM; ascorbic acid, $5 \times 10^{-6}$ M; disodium EDTA, $3 \times 10^{-5}$ M. This solution was oxygenated with 95% O$_2$, 5% CO$_2$ and maintained at 37° C.

Results $K_B$ for propranolol in guinea pig atria is $6.2 \times 10^{-10}$M.

$K_B$ for the compound of example 1 namely, 6,7-dichloro-1-(3,4,5-trimethoxybenzyl)-1,2,3,4,-tetrahydroisoquinoline is $6.7 \pm 2.3 \times 10^{-8}$M.

What is claimed is:

1. A compound of structure (I)

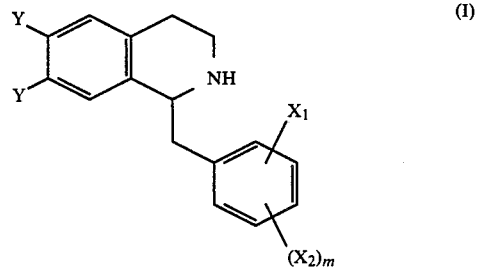

in which
Y is halogen;
X$_1$ is C$_{1-4}$ alkoxy;
m is 0 to 4; and X$_2$ is C$_{1-4}$ alkoxy, halogen or C$_{1-4}$ alkyl, provided that
  (i) when m is 1, 3 or 4, each X$_2$ is C$_{1-4}$ alkoxy; and,
  (ii) when m is 2, at least one X$_2$ is C$_{1-4}$
or a pharmaceutically acceptable acid addition salt thereof.

2. A compound as claimed in claim 1 in which m is 2.

3. A compound as claimed in claim 2 in which both groups X$_2$ are C$_{1-4}$ alkoxy.

4. A compound of structure (I) which is 6,7-dichloro-1-(3,4,5-trimethoxybenzyl)-1,2,3,4-tetrahydroisoquinolne.

5. A pharmaceutical composition comprising a compound of claim 1, in association with a pharmaceutically acceptable carrier.

6. A pharmaceutical composition as claimed in claim 8 in which the compound of claim 1 is 6,7-dichloro-1-(3,4,5-trimethoxybenzyl)-1,2,3,4-tetrahydroquinoline.

7. A method of producing β-adrenergic receptor antagonism in mammals that comprises administering internally to a subject in need of such inhibition an effective amount of a compound of claim 1.

8. The method of claim 7 in which the compound is 6,7-dichloro-1-(3,4,5-trimethoxybenzyl)-1,2,3,4-tetrahydroisoquinoline.

* * * * *